United States Patent [19]
Chen et al.

[11] Patent Number: 4,814,543
[45] Date of Patent: Mar. 21, 1989

[54] NITROGEN RESISTANT PARAFFIN HYDROISOMERIZATION CATALYSTS

[75] Inventors: Nai Y. Chen, Titusville; William E. Garwood, Haddonfield, both of N.J.; Sharon B. McCullen, Newtown, Pa.

[73] Assignee: Mobil Oil Corporation, New York, N.Y.

[21] Appl. No.: 138,749

[22] Filed: Dec. 28, 1987

[51] Int. Cl.$^4$ .............................................. C07C 5/13
[52] U.S. Cl. ................................................... 585/739
[58] Field of Search ........................................ 585/739

[56] References Cited

U.S. PATENT DOCUMENTS

| | | | |
|---|---|---|---|
| 4,016,218 | 4/1977 | Haag et al. | 585/467 |
| 4,016,245 | 4/1977 | Plank et al. | 423/328 |
| 4,016,246 | 4/1977 | Whittam | 423/329 |
| 4,076,842 | 2/1978 | Plank et al. | 423/328 |
| 4,229,282 | 10/1980 | Peters et al. | 208/111 |
| 4,247,388 | 1/1981 | Banta et al. | 208/111 |
| 4,257,872 | 3/1981 | La Pierre et al. | 208/59 |
| 4,284,529 | 8/1981 | Shihabi | 208/111 |
| 4,481,177 | 11/1984 | Valyocsik | 423/329 |
| 4,556,477 | 12/1985 | Dwyer | 208/111 |
| 4,605,488 | 8/1986 | Chester et al. | 208/111 |

FOREIGN PATENT DOCUMENTS 0102716 7/1983 European Pat. Off. .

Primary Examiner—Curtis R. Davis
Attorney, Agent, or Firm—Alexander J. McKillop; Charles J. Speciale; Malcolm D. Keen

[57] ABSTRACT

The present invention includes a process and catalyst composition for paraffinic isomerization of a hydrocarbon feedstock which has a paraffin content having no more than 20 carbon atoms per molecule. The feedstock is contacted with a crystalline aluminosilicate zeolite catalyst having pore openings defined by: (1) a ratio of sorption of n-hexane to o-xylene, on a volume percent basis, of greater than about 3, which sorption is determined at a $P/P_o$ of 0.1 and at a temperature of 50° C. for n-hexane and 80° C. for o-xylene and (2) by the ability of selectively cracking 3-methylpentane (3MP) in preference to the doubly branched 2,3-dimethylbutane (DMB) at 1000° F. and 1 atmosphere pressure from a 1/1/1 weight ratio mixture of n-hexane/3-methyl-pentane/2,3-dimethylbutane, with the ratio of rate constants $k_{3MP}/k_{DMB}$ determined at a temperature of 1000° F. being in excess of about 2, e.g., ZSM-22, ZSM-23, AXM-35 and mixtures thereof, in combination with a Group VIII metal, and having a zeolite $SiO_2/Al_2O_3$ ratio of at least about 20:1 at a temperature and pressure suitable for isomerization.

7 Claims, No Drawings

NITROGEN RESISTANT PARAFFIN HYDROISOMERIZATION CATALYSTS

BACKGROUND OF THE INVENTION

The present invention relates to the isomerization of paraffin containing hydrocarbon feedstock, and, in particular, to conversion by isomerization of n-paraffins, while maintaining a resistance to poisoning by nitrogen containing compounds.

Zeolite materials have been demonstrated to have catalytic properties for various types of hydrocarbon conversions. Certain zeolitic materials contain ordered, porous crystalline aluminosilicates having definitive crystalline structure, such as can be determined by X-ray diffraction, within which there are a large number of smaller cavities which may be interconnected by a number of still smaller channels or pores. The dimensions of these pores are such as to except for adsorption molecules of certain dimensions while rejecting those of larger dimensions. Furthermore, these materials may contain sites of reactivity to which the molecules can adhere or otherwise attach and be converted by, for example cracking, isomerizing, etc.

For example, in U.S. Pat. No. 4,257,872 to LaPierre, et al. there is disclosed a process for upgrading coke or gas oil by a low pressure catalytic hydrocracking of refractory hydrocarbon charge stocks. The Lapierre process contemplates initial hydrotreating of the refractory feed to convert sulfur, nitrogen and oxygen derivatives of hydrocarbon to hydrogen sulfide, ammonia and water while depositing metal contaminant from the hydrodecomposition of any organo-metal compounds. LaPierre, et al. indicate that the zeolites used therein have the ability to induce profound transformation of aliphatic hydrocarbons to aromatic hydrocarbons in commercially desirable yields and are generally highly effective in conversion reactors involving aromatic hydrocarbons. The process of LaPierre, et al. also contemplates the use of high pressure for purposes of hydrocracking the refractory hydrocarbon charge stocks, such as in the range of 100 to 3,000 psig. In fact, all of the pressures used in the examples shown therein include a pressure of at least a 1,000 psig.

In U.S. Pat. No. 4,247,388 to Banta, et al. a method is disclosed for improving catalytic hydrodewaxing of petroleum synthetic hydrocarbon feedstocks using acidic crystalline aluminosilicate zeolites such as those of the ZSM-5 type which involves treatment of the zeolites in order to adjust their initially high alpha activity to within a range of 55 to 150 alpha prior to use as catalysts in a hydrodewaxing operation.

In U.S. Pat. No. 4,229,282 to Peters, et al. an improved process for catalytically dewaxing a hydrocarbon oil is disclosed in which the waxy oil is contacted with a dense zeolitic dewaxing catalyst in the presence of hydrogen and in combination with a nickel-tungsten hydrogenation component. The dewaxed oil has good stability and low bromine number compared with prior-art processed oils. The process may be used to dewax crude oils, fuel oil fractions and lubricating oils.

U.S. Pat. No. 4,284,529 to Shihabi discloses a process for conversion of relatively heavy hydrocarbon streams to produce lower molecular weight materials in order to convert, for example, waxy crude petroleum in the field to products suitable for transmission by pipeline. The objective of "cracking" in the Shihabi '529 disclosure is to reduce the molecular weight number, and does not address the issue of isomerization in order to convert the paraffinic content of a hydrocarbon feedstock.

Thus, in the search to perfect an efficient process and catalyst, artisans in the area of hydrocarbon processing have begun to reject high pressure hydrodewaxing processes of the prior-art in order to achieve high distillate yield through hydroisomerization, and are engaged in searching for a truly low pressure isomerization procedure and poison resistant catalyst which will yield optimum distillate range hydrocarbon feedstock with an acceptably low pour point. Accordingly, the present invention has been discovered to provide a significant advancement in the search for such efficient procedure and catalyst.

SUMMARY OF THE INVENTION

The present invention is a process for paraffin isomerization of a hydrocarbon feedstock having a paraffinic content of molecules with not more than about 20 carbon atoms, and preferably no more than about 16 carbon atoms, which includes contacting the paraffin-containing feedstock with a crystalline aluminosilicate zeolite catalyst having pore openings defined by: (1) a ratio of sorption of n-hexane to o-xylene, on a volume percent basis, of greater than about 3, which sorption is determined at a $P/P_o$ of 0.1 and at a temperature of 50° C. for n-hexane and 80° C. for o-xylene and (2) by the ability of selectively cracking 3-methylpentane (3MP) in preference to the doubly branched 2,3-dimethylbutane (DMB) at 1000° F. and 1 atmosphere pressure from a 1/1/1 weight ratio mixture of n-hexane/3-methyl-pentane/2,3-dimethylbutane, with the ratio of rate constants $k_{3MP}/k_{DMB}$ determined at a temperature of 1000° F. being in excess of about 2. Suitable zeolites include ZSM-22, ZSM-23 and ZSM-35 zeolites and/or mixtures thereof.

The expression, "$P/P_o$", as utilized in the specification and the claims, is accorded its usual significance as described in the literature, for example, in "The Dynamical Character of Adsorption" by J. H. deBoer, 2nd Edition, Oxford University Press (1968) and is the relative pressure defined as the ratio of the partial pressure of sorbate to the vapor pressure of sorbate at the temperature of sorption. The ratio of the rate constants, $k_{3MP}/k_{DMB}$, is determined from 1st order kinetics, in the usual manner, by the following equation $$k = (1/T_c)\ln(1/1-\epsilon)$$

where k is the rate constant for each component, $T_c$ is the constant time and $\epsilon$ is the fractional conversion of each component.

The zeolite catalysts of the present invention also have deposited therein a Group VIII metal, and are characterized by a zeolite silica to alumina ratio of at least about 20:1. The procedure includes providing a temperature and pressure range suitable for isomerization, which is preferably at a temperature of no more than from about 390° F. to about 85020 F. and a pressure of from no more than about 100 to about 1,000 psig., and most preferably between about 250 to 600 psig.

The Group VIII metals which can be used in the catalyst of the present invention can be selected from the Group consisting of platinum, palladium, iridium, osmium, rhodium and ruthenium. The metal can be incorporated into the zeolite by ionic exchange up to a metal content in a range of from about 0.01% to about 10% by weight, and preferably from about 0.1% to about 3% by weight. The zeolite can be supported in a binder selected from one of silica, alumina, silica-alumina, and titania.

When the feedstock is distillate range feedstock, which is generally considered as having a boiling point of from about 330° F. to about 650° F., the catalyst of the present invention has been shown to resist poisoning by nitrogenous compounds. Since the catalyst of the present invention is resistant to poisoning by such nitrogen-containing molecules under isomerization conditions, it is particularly useful for conversion of distillate range feedstock.

Furthermore, a hydrocarbon feedstock having a substantial paraffinic content can be converted to reduce the boiling point 10° or 20° F. without the unwanted side effects of significant cracking which normally results from high temperature, high pressure procedures in the presence of a zeolitic catalyst. As a result, the feedstock can be treated without significant reduction of distillate range yield. The product resulting from this process contains a significantly greater amount of isoparaffinic compounds, i.e., branched hydrocarbon chains, than straight hydrocarbon chains. This is unlike the product resulting from hydrocracking processes which includes a greater amount of straight chain molecules. Consequently, the yield of nonparaffinic distillate is significantly increased.

Thus, while other procedures have been found to be useful in reducing the paraffinic content by hydrocracking, the present invention has been found to be unexpectedly efficient in reducing the n-paraffin content by hydroisomerization while maintaining high distillate range yields.

For a better understanding of the present invention, together with other and further objects, reference is made to the following description, and the scope will be pointed out in the appended claims.

DETAILED DESCRIPTION OF THE INVENTION

The present invention is a process and catalyst for isomerizing the paraffins of a hydrocarbon feedstock A catalyst prepared in accordance with the present invention includes a special group of crystalline aluminosilicate zeolites having pore openings defined by: (1) a ratio of sorption of n-hexane to o-xylene, on a volume percent basis, of greater than 3, which sorption is determined at a $P/P_o$ of 0.1 and a temperature of 50° C. for n-hexane and 80° C. for o-xylene and (2) by the ability of selectively cracking 3-methylpentane (3MP) in preference to the doubly branched 2,3-dimethylbutane (DMB) at 1000° F. and 1 atmosphere pressure from a 1/1/1 weight ratio mixture of n-hexane/3-methyl-pentane/2,3-dimethylbutane, with the ratio of rate constants $k_{3MP}/k_{DMB}$ determined at a temperature of 1000° F. being in excess of about 2. Suitable zeolites for use in the present invention include ZSM-22, ZSM-23 and ZSM-35 and/or mixtures thereof. The quantities $P/P_o$ and $K_{3MP}/K_{DMD}$ are defined above.

The acidity of the zeolites of the present invention are reduced and a Group VIII metal is incorporated therein. These catalysts are effective for the isomerization of n-paraffins and are resistant to nitrogen poisons, especially those found in distillate range fedstocks, as a result of their specific pore size openings which are effective to exclude most nitrogen containing organic molecules from entering therein. Inasmuch as the medium pore zeolites have in the past been considered as somewhat limited for purposes of isomerization as a result of their pore size, the present invention provides an unexpectedly efficient procedure and catalyst for effectively isomerizing paraffinic feedstocks, especially in hydrocarbon distillate range feedstock having nitrogen poisons.

The group of medium pore zeolites of the present invention include ZSM-22, ZSM-23, and ZSM-35. These catalysts are generally considered to be medium pore catalysts based on the measure of its internal structure as represented by its Constraint Index. Zeolites which provide highly restricted access to and egress from its internal structure have a high value for the Constraint Index, while zeolites which provide relatively free access to the internal zeolite structure have a low value for their Constraint Index. The method for determining Constraint Index is described fully in U.S. Pat. No. 4,016,218 which is incorporated herein by reference.

Those zeolites exhibiting a Constraint Index value within the range of from about 1 to about 12 are considered to be medium pore zeolites. Zeolites which are considered to be in this range include ZSM-5, ZSM-11, etc. Upon careful examination of the medium pore zeolites, however, it has been found that not all of them are as efficient as a catalyst for isomerization of a paraffin-containing feedstock having no greater than n-$C_{20}$ molecules, and preferably molecules having no greater than an n-$C_{16}$ chain. In particular, it has been found that the group including ZSM-22, ZSM-23, and ZSM-35 used in combination with Group VIII metals can provide a procedure whereby a distillate range hydrocarbon feedstock having a paraffinic content with molecules of 20 carbon atoms or less undergoes unexpectedly efficiently isomerization without destroying the ultimate distillate range yield of the feedstock.

It is known to use prior-art techniques for formation of a great variety of synthetic aluminosilicates. These aluminosilicates have come to be designated by letter or other convenient symbols. One of the zeolites of the present invention, ZSM-22, is a highly silaceous material which includes crystalline three-dimensional continuous framework silicon containing structures or crystals which result when all the oxygen atoms in the tetrahedra are mutually shared between tetrahedral atoms of silicon or aluminum, and which can exist with a network of mostly $SiO_2$, i.e., exclusive of any intracrystalline cations. The description of ZSM-22 is set forth in full in U.S. Pat. No. 4,556,477, U.S. Pat No 4,481,177, and European Patent Application No. 102,716 the contents of which are incorporated herein by reference.

As indicated in U.S. Pat. No. 4,566,477 the crystalline material ZSM-22 has been designated with a characteristic X-ray diffraction pattern as set forth in Table I.

TABLE I

| Most Significant Lines of ZSM-22 | |
|---|---|
| Interplanar d-spacings (A) | Relative Intensity (I/Io) |
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |

TABLE I-continued

| Most Significant Lines of ZSM-22 | |
|---|---|
| Interplanar d-spacings (A) | Relative Intensity (I/Io) |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in Angstroms, corresponding to the recorded lines, were determined. In Table I, the relative intensities are given in terms of the symbols vs=very strong, s=strong, m=medium, w=weak, etc. It should be understood that the X-ray diffraction pattern is characteristic of all the species of ZSM-22 zeolite compositions. Ion exchange of the alkali metal cations with other ions results in a zeolite which reveals substantially the same X-ray diffraction pattern with some minor shifts in interplanar spacing and variation in relative intensity.

Furthermore, the original cations of the as-synthesized ZSM-22 can be replaced at least in part by other ions using conventional ion exchange techniques. It may be necessary to precalcine the ZSM-22 zeolite crystals prior to ion exchange. In accordance with the present invention, the replacement ions are those taken from Group VIII of the Periodic Table, especially platinum, palladium, iridum, osmium, rhodium and ruthenium.

ZSM-22 freely sorbs normal hexane and has a pore dimension greater than about 4 Angstroms. In addition, the structure of the zeolite provides constrained access to larger molecules. The Constraint Index as determined by the procedure set forth in U.S. Pat. No. 4,016,246 for ZSM-22 has been determined to be from about 2.5 to about 3.0.

The ZSM-22 can be incorporated with other material resistant to the temperatures and other conditions employed in organic conversion processes. Such materials include active and inactive materials and synthetic or naturally occurring zeolites as well as inorganic material such as clays, silica and/or metal oxides. The clays, silica and/or metal oxides may be either naturally occurring or in the form of gellates precipitates or gels including mixtures of silica and metal oxides. The ZSM-22 can be composited with naturally occurring clays such as montmorillonite and kaolin family, or with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The relative proportions of finally divided crystalline material and inorganic oxide gel matrix can vary, with the crystal content ranging from about 1 to about 90% by weight.

Another zeolite which can be used with the present invention is the synthetic crystalline aluminosilicate referred to as ZSM-23, disclosed in U.S. Pat. No. 4,076,842, the contents of which are incorporated herein by reference. The ZSM-23 composition has a characteristic X-ray diffraction pattern as set forth herein in Table II.

TABLE II

| d (A) | $I/I_o$ |
|---|---|
| 11.2 ± 0.23 | M |
| 10.1 ± 0.20 | W |
| 7.87 ± 0.15 | W |
| 5.59 ± 0.10 | W |
| 5.44 ± 0.10 | W |
| 4.90 ± 0.10 | W |
| 4.53 ± 0.10 | S |
| 3.90 ± 0.08 | VS |
| 3.72 ± 0.08 | VS |
| 3.62 ± 0.07 | VS |
| 3.54 ± 0.07 | M |
| 3.44 ± 0.07 | S |
| 3.36 ± 0.07 | W |
| 3.16 ± 0.07 | W |
| 3.05 ± 0.06 | W |
| 2.99 ± 0.06 | W |
| 2.85 ± 0.06 | W |
| 2.54 ± 0.05 | M |
| 2.47 ± 0.05 | W |
| 2.40 ± 0.05 | W |
| 2.34 ± 0.05 | W |

The ZSM-23 composition can also be identified in terms of smaller ratios of oxides in the anhydrous state as follows:

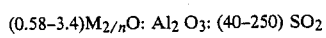

$$(0.58-3.4)M_{2/n}O: Al_2O_3: (40-250) SO_2$$

wherein M is at least 1 cation and N is the valence thereof. As in the ZSM-22, the original cations of as-synthesized ZSM-23 can be replaced in accordance with techniques well-known in the art, at least in part by ionic exchange with other cations. In the present invention these cations include the Group VIII metals as set forth hereinbefore.

The third medium pore zeolite which has been found to be successful in the present invention is ZSM-35, which is disclosed in U.S. Pat. No. 4,016,245, the contents of which are incorporated herein by reference. The synthetic crystalline aluminosilicate known as ZSM-35, has a characteristic X-ray diffraction pattern which is set forth in U.S. Pat. No. 4,016,245. ZSM-35 has a composition which can be identified in terms of small ratio of oxides in the anhydrous state as follows:

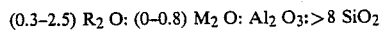

$$(0.3-2.5) R_2O: (0-0.8) M_2O: Al_2O_3: >8 SiO_2$$

wherein R is an organic nitrogen-containing cation derived from ethylenediamine or pyrrolidine and M is an alkali metal cation. The original cations of the as-synthesized ZSM-35 can be replaced with techniques well known in the art which includes ion exchange with other cations. In the present invention the cation exchange is used to replace the as-synthesized cations with the Group VIII metals set forth herein. It has been observed that the X-ray diffraction pattern of ZSM-35 is similar to that of natural ferrierite with a notable exception being that natural ferrierite patterns exhibit a significant line at 1.33 A.

EXAMPLES

The present invention includes a catalyst for paraffin isomerization which includes incorporating a noble metal or Group VIII metal into a select group of crystalline aluminosilicate zeolites. In particular, the zeolites used herein are ZSM-22, ZSM-23, and ZSM-35 Each of the zeolites used in these examples, have been prepared with a silica to alumina ratio $SiO_2/Al_2O_3$ greater than or equal to 20:1.

The metal has been incorporated into the zeolite by ion exchange to metal contents in the range of 0.01 to 10% by weight, but preferably in a range of from 0.1 to 3 weight percent. In addition to preparation of the zeolites of the present invention, ZSM-5 was prepared in order to compare the isomerization selectivity.

EXAMPLE 1

The isomerization selectivity of Pt/ZSM-5/$Al_2O_3$ was measured using N-hexadecane at 500 psi, 531° F., $H_2$/HC=13.1 and 1 liquid hourly space velocity (LHSV) The isomerization selectivity has been defined as the ratio of the i-$C_{16}$ yield and the n-$C_{16}$ conversion. At 77% n-$C_{16}$ conversion the isomerization selectivity was only 0.30. Benzoquinoline was then added to the n-$C_{16}$ feed in an amount to obtain 20 ppm nitrogen. It was necessary to increase the reactor temperature 54° F. to maintain the n-$C_{16}$ conversion at 77 wt. %. The isomerization selectivity increased to 0.43.

EXAMPLE 2

The isomerization selectivity of Pt/ZSM-22/$Al_2O_3$ was measured as described in Example 1. 85 wt. % conversion of n-$C_{16}$ was obtained at 576° F. and the isomerization selectivity was 0.76. When 20 ppm nitrogen was added as benzoquinoline, the reactor temperature was increased 52° F. to maintain conversion, no change in isomerization selectivity was observed. This catalyst shows better isomerization selectivity compared to ZSM-5 for a clean feed and in the presence of a nitrogen poison.

EXAMPLE 3

The performance of Pt/ZSM-23/$Al_2O_3$ for isomerization was tested as described in Example 1. At 608° F., 69 wt. % conversion of n-$C_{16}$ was observed with 0.60 isomerization selectivity. The reactor temperature was increased only 36° F. to maintain the n-$C_{16}$ conversion after benzoquinoline was added. This catalyst shows higher isomerization selectivity and better nitrogen resistance compared to Pt/ZSM-5/$Al_2O_3$ in Example 1.

EXAMPLE 4

Pt/ZSM-35/$Al_2O_3$ was used to isomerize n-$C_{16}$ at the conditions described in Example 1. 76 wt. % n-$C_{16}$ conversion was observed at 585° F. with 0.50 isomerization selectivity. when 20 ppm nitrogen as benzoquinoline was added the reactor temperature was increased by 108° F. to maintain conversion, however, the isomerization selectivity increased to 0.70. Although a larger temperature increase was required to maintain n-$C_{16}$ conversion activity compared to Pt/ZSM-5/$Al_2O_3$, the isomerization selectivity was much higher for Pt/ZSM-35/$Al_2O_3$ for a clean feed and for a feed containing nitrogen.

TABLE III

|  | Example 1 | Example 2 | Example 3 | Example 4 |
| --- | --- | --- | --- | --- |
| n-$C_{16}$ Conversion w/o Nitrogen | 77% | 85% | 69% | 76% |
| n-$C_{16}$ Conversion w/Nitrogen | 77% | 85% | 69% | 76% |
| i-$C_{16}$* Selectivity w/o Nitrogen | 0.30 | 0.76 | 0.60 | 0.50 |
| i-$C_{16}$ Selectivity w/Nitrogen | 0.43 | 0.76 | 0.60 | 0.70 |

*Isomerization selectivity is defined as the ratio of the i-$C_{16}$ yield to the n-$C_{16}$ conversion.

Thus, while there had been described what are presently belived to be the preferred embodiments of the present invention, other modifications and changes will become apparent to those skilled in the art and it is intended to claim all such changes which come within the true scope of the invention.

What is claimed is:

1. A process for paraffin isomerization of a distillate range hydrocarbon feedstock having a boiling range of from about 330° F.–650° F. and a paraffinic content of molecules with not more than about 20 carbon atoms, and containing nitrogen impurities of at least 20 ppm, comprising:

contacting said paraffin-containing feedstock with a catalyst including a crystalline zeolite catalyst having pore openings defined by: (1) a ratio of sorption of n-hexane to o-xylene, on a volume percent basis, of greater than about 3, which sorption is determined at a $P/P_o$ of 0.1 and at a temperature of 50° C. for n-hexane and 80° C. for o-xylene and (2) by the ability of selectively cracking 3-methylpentane (3MP) in preference to the doubly branched 2,3dimethylbutane (DMB) at 1000° F. and 1 atmosphere pressure from a 1/1/1 weight ratio mixture of n-hexane/3-methyl-pentane-2,3dimethylbutane, with the ratio of rate constants $k_{3MP}/k_{DMB}$ determined at a temperature of 1000° F. being in excess of about 2, said catalyst including a Group VIII metal, and having a zeolite $SiO_2/Al_2O_3$ ratio of at least about 20:1, said contacting made at a temperature of from about 390° F. to about 850° F. and a pressure of from about 100 psig to about 1,000 psig.

2. The process of claim 1 wherein said crystalline aluminosilicate catalyst is selected from the group consisting of ZSM-22, ZSM-23, and ZSM-35.

3. The process of claim 1 wherein said Group VIII metal is selected from the group consisting of Pt, Pd, Ir, Os, Rh and Ru.

4. The process of claim 1 wherein said metal is incorporated into said zeolite by ion exchange to a metal content in the range of from about 0.01% to about 10.0% by weight.

5. The process of claim 3 wherein said metal content is from about 0.1% to about 3.0% by weight.

6. The process of claim 1 wherein said zeolite is supported in a binder selected from one of silica, alumina, silica-alumina, and titania.

7. The process of claim 1 wherein said paraffin content has molecules of no greater than about 16 carbon atoms.

* * * * *